United States Patent [19]

Bockow et al.

[11] Patent Number: 5,411,988
[45] Date of Patent: May 2, 1995

[54] COMPOSITIONS AND METHODS FOR INHIBITING INFLAMMATION AND ADHESION FORMATION

[76] Inventors: Barry I. Bockow, 16122-8th Ave. S.W., Ste. D3, Seattle, Wash. 98166; Marc D. Erlitz, 12034 NE. 130th La. #101, Kirkland, Wash. 98034

[21] Appl. No.: 144,054

[22] Filed: Oct. 27, 1993

[51] Int. Cl.⁶ ............... A61K 31/20; A61K 31/61; A61K 31/07
[52] U.S. Cl. ............... 514/560; 514/163; 514/725
[58] Field of Search ............... 514/163, 549, 560, 725

[56] References Cited

U.S. PATENT DOCUMENTS

| | | | |
|---|---|---|---|
| 3,943,248 | 3/1976 | Shulman | 424/196 |
| 4,526,902 | 7/1985 | Rubin | 514/560 |
| 4,607,052 | 8/1986 | Mendy et al. | 514/547 |
| 4,816,271 | 3/1989 | Scaffidi | 424/60 |
| 4,843,095 | 6/1989 | Rubin | 514/558 |
| 4,847,071 | 7/1989 | Bissett | 424/59 |
| 4,855,138 | 8/1989 | Trenzeluk | 424/195.1 |
| 4,857,328 | 8/1989 | Trenzeluk | 424/195.1 |
| 4,937,254 | 6/1990 | Sheffield et al. | 514/420 |
| 4,938,984 | 7/1990 | Traitler et al. | 426/580 |
| 4,954,332 | 9/1990 | Bissett | 424/59 |
| 4,963,380 | 10/1990 | Schroeder et al. | 426/330.3 |
| 5,059,622 | 10/1991 | Sears | 514/549 |
| 5,104,655 | 4/1992 | Bombardelli et al. | 424/195.1 |
| 5,178,873 | 1/1993 | Horrobin et al. | 424/422 |
| 5,234,952 | 8/1993 | Crozier-Willi et al. | 514/558 |

FOREIGN PATENT DOCUMENTS

WO91/16914  11/1991  WIPO.

OTHER PUBLICATIONS

Martindale The Extra Pharmacopoeia, 28th ed., (1982), The Pharmaceutical Press, London, pp. 235–243.
The Nutrition Desk Reference, (1987) Garrison et al. Keats Publishing, Inc., New Canhan, Conn. p. 89.
Anderson's *Pathology*, 9th Edition, ed., John M. Kissane, M.D., The C.V. Mosby Company, pp. 67–110, 1990.

*Primary Examiner*—Raymond Henley, III
*Attorney, Agent, or Firm*—Seed and Berry

[57] ABSTRACT

There is disclosed compositions and methods for inhibiting inflammation and/or adhesion formation in a patient. The compositions comprise omega-3 and/or omega-6 fatty acids, a nonionic surfactant, and a pharmaceutically acceptable carriers or diluents. The omega fatty acid compositions may optionally contain cyclooxygenase inhibitors and other additives and preservatives such as dextrose and vitamin A. The methods of inhibiting inflammation and/or adhesion formation in a patient comprise administration of an effective quantity of a composition to a body cavity of the patient.

24 Claims, No Drawings

COMPOSITIONS AND METHODS FOR INHIBITING INFLAMMATION AND ADHESION FORMATION

TECHNICAL FIELD

This invention relates generally to compositions and methods for inhibiting inflammation and/or adhesion formation in patients and, more specifically, to compositions containing omega fatty acids and methods for their administration.

BACKGROUND OF THE INVENTION

The prevention or inhibition of inflammation and adhesion formation is of significant concern to medical professionals.

Adhesion formation is a final common physiological result of inflammation from any cause. Although it is commonly seen following surgery, it can also occur in many other clinical settings. In the post-operative setting, serious scar and/or adhesion formation can occur, greatly increasing patient morbidity. If this serious complication could be avoided, great savings could be realized in health care costs by reducing the need for future hospitalizations and therapeutic interventions. Furthermore, if adhesion formation is prevented, many chronic diseases could be prevented or at least mitigated.

In response to any tissue injury, the body will attempt to heal itself. The manner in which the body responds to an initial injury can frequently determine whether a person will return to normal health or develop significant chronic disease. For example, adhesions are an undesirable biological response to tissue injury. They sometimes occur post-operatively, but may also occur after other forms of injury such as infection and trauma.

The healing process is mediated by the immune response. The immune system is a protective network that enables the body to ward off disease. For example, a microorganism, such as a bacteria or virus, can invade the body and thereby activate the immune system. Under normal circumstances, the host is protected when the invading microorganism is eliminated.

The body's host mechanism, in attempting to heal areas of injury, sometimes mounts an overly aggressive immune response. This undesirable reaction can lead to scar formation and/or adhesions. This "hyper" immune response is also the cause of a group of illnesses known as "autoimmune" diseases which include rheumatoid arthritis, systemic lupus erythematosis, thyroiditis, inflammatory bowel disease, allergies, and many chronic dermatologic diseases such as psoriasis and eczema. Recently researchers have presented evidence that atherosclerosis or "hardening of the arteries" is also mediated via this "hyper" immune response.

Often the immune response is associated with increased blood flow and increased vascular permeability. This causes the release of white blood cells, macrophages, platelets and other cellular elements to the surrounding tissues. These cells are the harbingers of inflammation. By blocking or restricting the immune response and by inhibiting certain cellular functions, the formation of excessive scar tissue can be inhibited. While adhesion formation results to some extent for all large inflammations or in instances where marked cell damage has occurred, adhesion formation generally results from an overly aggressive immune response mounted by the host in an attempt to heal the injured tissue.

Prostaglandins are a family of compounds which have been identified as playing a significant role in inflammation. Their biosynthesis is triggered by the release of arachidonic acid, a preliminary event in the immune response. Prostaglandins are produced throughout the body and are derived from enzymatic action on a common substrate, arachidonic acid. The first step in prostaglandin synthesis is the oxygenation of arachidonic acid by the enzyme cyclooxygenase. The oxygenated prostaglandin precursors are subject to further enzymatic processes which provide the various members of the prostaglandin family.

Closely related in structure and function to the prostaglandins are a family of compounds known as leukotrienes. Leukotrienes are also derived from arachidonic acid metabolism, but through the lipoxygenase pathway. Like prostaglandins, leukotrienes exhibit inflammatory properties.

Arachidonic acid is an essential fatty acid consisting of twenty carbon atoms and containing four carbon-carbon double bonds. By virtue of the position of the carbon-carbon double bond at the methyl (omega) end of the hydrocarbon chain, it is classified as an omega-6 fatty acid. A closely related family of fatty acids are the omega-3 fatty acids. In addition to double bond position, omega-6 and omega-3 fatty acids may also be distinguished by their origins. The precursors to these fatty acids are derived from botanical and/or marine plants which are in turn further metabolized in animals to provide the long chain polyunsaturated acids. Omega-6 fatty acids may be found predominantly in land animals, while omega-3 fatty acids are abundant in fish.

In principle, any immune response may be modulated by stimulation or suppression—that is, immunomodulation may be accomplished through the use of immunostimulants or immunosuppressants (collectively referred to as immunomodulators). Therefore, immunomodulators may be effective in treating inflammatory conditions and preventing adhesion formation.

To this end, it is believed that inhibition of the enzymatic pathways which yield prostaglandins and leukotrienes would result in decreased production of these compounds and a consequent reduction in their inflammatory effects. The inhibitors of these enzymatic pathways are thus immunomodulators of the immune response.

As mentioned above, adhesion formation has been attributed to overly aggressive immune response. One class of compounds which has been identified as immunostimulants are interleukins. Interleukins are soluble immuno-enhancing glycoproteins produced by T-lymphocytes and have been commonly utilized as treatments to restore and/or bolster immune response in immunodeficient conditions. Accordingly, compounds which inhibit interleukin production are also immunomodulators. Such inhibitors are believed to suppress interleukin production and, consequently, immune response thereby effectively inhibiting both inflammation and adhesion formation.

Despite the great need to inhibit adhesion formation, current therapeutic options and preventive measures are of little or limited effectiveness. Accordingly, there is a need in the art for compositions which effectively modulate immune response and prevent, inhibit, or provide treatment for inflammation and adhesion formation. The present invention fulfills these needs, and provides further related advantages.

SUMMARY OF THE INVENTION

Briefly stated, the present invention is directed to compositions and methods for inhibiting inflammation and adhesion formation in warm-blooded animals, including humans (hereinafter referred to as patients) and, more specifically, to compositions containing omega fatty acids and methods for their administration.

In one aspect of this invention, compositions which contain omega fatty acids are disclosed. In one embodiment, a composition comprising an omega-3 fatty acid (a fatty acid derived from marine origins) is disclosed. The composition contains therapeutically effective amounts of the omega-3 fatty acid in combination with a nonionic surfactant and one or more acceptable carriers and/or diluents.

In another embodiment, a composition comprising an omega-6 fatty acid (a fatty acid derived from botanical origins) is disclosed. The composition contains therapeutically effective amounts of the omega-6 fatty acid in combination with a nonionic surfactant and one or more acceptable carriers and/or diluents.

In a further embodiment, a composition comprising both an omega-3 and an omega-6 fatty acid is disclosed. The composition contains therapeutically effective amounts of the omega-3 and omega-6 fatty acids in combination with a nonionic surfactant and one or more acceptable carriers and/or diluents.

The omega fatty acid compositions of the present invention may further comprise cyclooxygenase inhibitors and other additives and preservatives such as dextrose and vitamin A.

In another aspect of the invention, methods for inhibiting inflammation and adhesion formation in a patient are disclosed. These methods comprise administration of an effective quantity of the compositions of the present invention to a body cavity of the patient.

Other aspects of the present invention will become evident upon reference to the following detailed description.

DETAILED DESCRIPTION OF THE INVENTION

The present invention is generally directed to compositions and methods for inhibiting inflammation and adhesion formation in patients and, more specifically, to compositions containing omega fatty acids derived from marine and/or botanical sources, as well as methods for their administration. In addition to an omega fatty acid, the compositions of the present invention also contain a nonionic surfactant and a pharmaceutically acceptable carrier or diluent.

Although not intending to be limited to the following theory, it is believed that the compositions of the present invention effectively inhibit the syntheses of biochemicals which are ultimately responsible for inflammation and adhesion formation. In inflammation, these biochemicals include prostaglandins and leukotrienes, and for adhesion formation, the biochemicals include interleukins. The omega fatty acids of the compositions of the present invention inhibit the above-mentioned prostaglandin and leukotriene syntheses through interference with the cyclooxygenase and lipoxygenase pathways, respectively, and also inhibit interleukin production. Interleukin-2 is a potent mediator of the inflammatory response. Therapeutic measures that lower interleukin levels are associated with a decreased inflammatory response and often improved clinical outcome. Competitive inhibition by the omega fatty acids of the compositions of the present invention interferes with the utilization of arachidonic acid in both cyclooxygenase and lipoxygenase pathways, and renders the production of prostaglandins and leukotrienes largely inoperative. The same competitive inhibition principle applies to the diminution of interleukin production by the omega fatty acids of the compositions of the present invention.

Fatty acids are a class of organic compounds that are characterized by a long hydrocarbon chain terminating with a carboxylic acid group. Fatty acids have a carboxyl end and a methyl (i.e., "omega") end. Omega-3 fatty acids are derived from marine sources, while omega-6 fatty acids are derived from botanical sources. In addition to the difference in their origins, these omega fatty acids may be distinguished based on their structural characteristics.

Omega-3 fatty acids are a family of polyunsaturated fatty acids where the unsaturated carbon most distant from the carboxyl group is the third carbon from the methyl terminus. Omega-3 fatty acids have the following general formula:

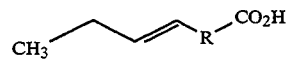

where R is a saturated or unsaturated, substituted or unsubstituted, branched or straight chain alkyl group having from 1 to 20 carbon atoms. Preferably, R is an unsaturated straight chain alkyl having from 13 to 17 carbon atoms (i.e., an omega-3 fatty acid having from 18 to 22 total carbon atoms), and containing from 2 to 6 carbon-carbon double bonds. In a preferred embodiment, the compositions of the present invention comprise omega-3 fatty acids which contain 20 carbon atoms with 5 carbon-carbon double bonds, or 22 carbon atoms with 6 carbon-carbon double bonds, including (but not limited to) eicosapentaenoic acid ("EPA") and docosahexaenoic acid ("DHA"):

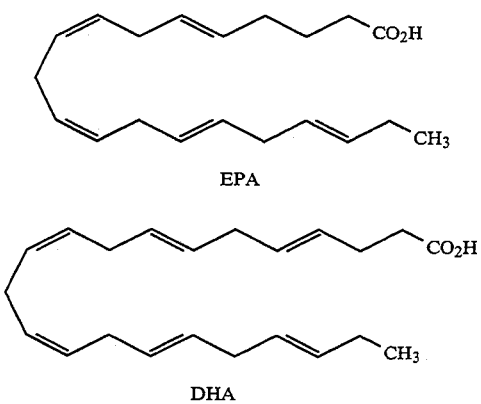

Similarly, omega-6 fatty acids are a family of unsaturated fatty acids where the unsaturated carbon most distant from the carboxyl group is the sixth carbon from the methyl terminus. Omega-6 fatty acids have the following general formula:

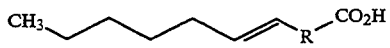

where R is a saturated or unsaturated, substituted or unsubstituted, branched or straight chain alkyl group having from 1 to 20 carbon atoms. Preferably, R is an unsaturated straight chain alkyl having from 10 to 14 carbon atoms (i.e., an omega-6 fatty acid having from 18 to 22 total carbon atoms), and containing from 2 to 6 carbon-carbon double bonds. In a preferred embodiment, the compositions of the present invention comprise omega-6 fatty acids which contain 18 carbon atoms with 3 carbon-carbon double bonds, or 20 carbon atoms with 4 carbon-carbon double bonds, including (but not limited to) gamma-linolenic acid ("GLA") and dihomo-gamma-linolenic acid ("DHGLA"):

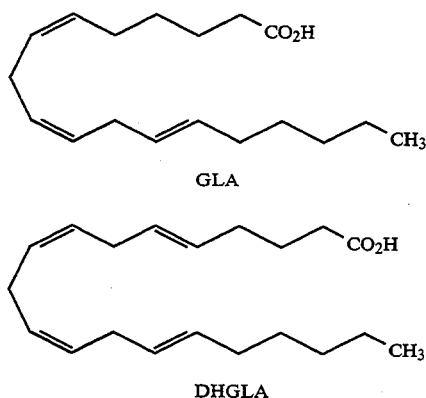

As mentioned above, the omega fatty acid compositions of the present invention may comprise omega-3 fatty acids or omega-6 fatty acids or a combination of omega-3 and omega-6 fatty acids. The omega fatty acids are present in the compositions in amounts sufficient to inhibit inflammation and adhesion formation in a patient when administered to a body cavity thereof. Moreover, a single omega fatty acid may be employed, or a mixture of two or more omega fatty acids may be used. For example, the compositions of the present invention may contain a single omega-3 or omega-6 fatty acid, two or more omega-3 or omega-6 fatty acids, an omega-3 fatty acid and one or more omega-6 fatty acids, an omega-6 fatty acid and one or more omega-3 fatty acids, or two or more omega-3 fatty acids and two or more omega-6 fatty acids.

In addition to omega fatty acids, the compositions of the present invention contain a nonionic surfactant. The nonionic surfactant of the composition facilitates the effective administration of the omega fatty acids to the tissues of the body cavity under treatment. The surfactant solubilizes the omega fatty acid and also acts as an emulsifying and/or dispersing agent which increases the permeability of the tissues toward the omega fatty acid of the composition. Preferred nonionic surfactants include polyethylene fatty acid esters and polysorbates.

The omega fatty acid compositions of the present invention may further comprise cyclooxygenase inhibitors and other additives and preservatives such as dextrose and vitamin A.

Cyclooxygenase inhibitors of the compositions of the present invention include any compound which effectively inhibits cyclooxygenase, including (but not limited to) acetylating and non-acetylating inhibitors. Cyclooxygenase inhibitors which acetylate cyclooxygenase (i.e., "acetylating inhibitors") include acetylsalicylic acid (aspirin) and salicylsalicylic acid, as well as salts thereof. Cyclooxygenase inhibitors which do not acetylate cyclooxygenase (i.e., "non-acetylating inhibitors") include (but are not limited to) salicylates such as salicylic acid, trilisate, and diacid, and salts thereof. Other cyclooxygenase inhibitors include naproxen, piroxicam, indomethacin, sulindac, meclofenamate, diflunisal, tolmetin, phenylbutazone, ibuprofen, fenoprofen, ketoprofen and nabumetone.

The cyclooxygenase inhibitors are present in the composition in amounts sufficient to inhibit inflammation and adhesion formation in a patient when administered to a body cavity of the patient in combination with the omega fatty acid. A single cyclooxygenase inhibitor may be employed, or a mixture of two or more different inhibitors may be used.

The compositions of the present invention may also contain other additional optional ingredients including but not limited to, vitamin A and dextrose. These components provide composition stability and body cavity tissue permeability.

For purposes of administration, the compositions of the present invention may be formulated in any suitable manner for application to the tissues of the body cavity which are to be treated. Such formulations contain effective amounts of the omega fatty acid and nonionic surfactant, as well as one or more pharmaceutically acceptable carriers or diluents. More specifically, the formulations of the present invention may be administrated in the form of liquids containing acceptable diluents such as saline and sterile water, or may be administered as suspensions, emulsions or gels containing acceptable diluents or carriers to impart the desired texture, consistency, viscosity and appearance. Such acceptable diluents and carriers are familiar to those skilled in the art and include (but are not limited to) fatty alcohols, fatty acids, fatty esters, organic and inorganic bases, steroid esters, triglyceride esters, phospholipids such as lecithin and cephalin, polyhydric alcohol esters, hydrophobic lanolin derivatives, hydrocarbon oils, cocoa butter waxes, silicon oils, preserving agents, pH balancers and cellulose derivatives. One skilled in the art may further formulate the omega fatty acid and nonionic surfactant in an appropriate manner, and in accordance with accepted practices, such as those disclosed in *Remington's Pharmaceutical Sciences*, Gennaro, Ed., Mack Publishing Co., Easton, Pa. 1990 (which is incorporated herein by reference in its entirety).

As mentioned above, the omega fatty acid and nonionic surfactant are present in the composition in an amount sufficient to inhibit inflammation and adhesion formation in a patient when administered to a body cavity of the patient. When formulated for such administration, the omega fatty acid may be present in an amount ranging from 5% to 60% by weight (based on the total weight of the formulation), more preferably from 20% to 60% by weight, and most preferably from 35% to 60%. Similarly, the nonionic surfactant may be present in an amount ranging from 1% to 15%, more preferably from 2% to 10%, and most preferably from 3% to 5%.

Further optional ingredients include a cyclooxygenase inhibitor optionally present in an amount ranging from 0.5% to 1% by weight, vitamin A optionally present in an amount ranging from 1% to 2% by weight, and dextrose optionally present in an amount ranging from 2% to 4% by weight. Example 1 illustrates representative formulations of the compositions of the present invention.

The compositions of the present invention are administered to the tissues of the body cavity of a patient to inhibit inflammation and/or adhesion formation. As used herein, a body cavity is any space or potential space within the body. Examples of suitable body cavities to which the compositions may be administered include the following cavities: oral, abdominal, pleural, thoracic, pericardial, joint, rectal, bladder, and tympanic.

Accordingly, the compositions of the present invention may be used to treat active inflammatory conditions, including active diseases or more chronic, subacute diseases. For example, the compositions may be used in the treatment of both the early and late stages of inflammatory arthritis, inflammatory bowel disease, pericarditis, peritonitis, and pleuritis. The compositions may also be administered for dental applications. For example, the compositions are useful in preventing inflammation after tooth extraction or for treating various forms of gum disease. More specifically, after a periodontist performs gum surgery, an amount of the composition in liquid form may be applied directly to the wound, or may be used to bathe the inflamed tissues as a rinse. Alternatively, the composition may be applied daily in the form of a gel directly on the inflamed tissue for an effective period of time (such as one to two weeks following surgery). The compositions are also useful in inhibiting adhesion formation during intracavitary surgery and arthoscopy.

The compositions of this invention may be administered in liquid form by instillation into a body cavity directly at the time of surgery, thoracoscopy, laparoscopy, arthroscopy, cystoscopy, injection, or other procedure. The composition may also be applied directly to the lung, pericardium, synovium, tympanic membrane, or abdominal organs. Following application, the composition may be left to bathe the aforementioned organs, or removed by suction after having been lavaged within the cavity. Depending upon the anatomic site involved and the patient's clinical condition, additional applications may be employed.

The compositions of the present invention may be applied to a body cavity to inhibit inflammation under the following representative conditions. A patient with chronic synovitis of the knee may be injected or instilled with the composition into the knee three or four times a year. A patient with adhesive capsulitis of the shoulder would also benefit by administration of the composition after manipulation of the shoulder under anesthesia. A patient with chronic inflammatory lung disease may have the composition injected into the pleural space 6–12 times a year (depending upon the patient's clinical course). A patient with interstitial cystitis (chronic inflammation of the bladder) may have the composition administered via a cystoscope or urinary catheter 6–12 times a year. A patient with chronic inflammatory bowel disease which has an ulcerated and hemorrhagic intestinal mucosa may receive an annual lavage at the time of colonoscopy (e.g., the composition is dispersed through the entire colon as the colonoscope is slowly removed).

The compositions of the present invention may also be applied to a body cavity to inhibit adhesion formation under the following representative conditions. A patient undergoing laparotomy (surgery of the abdominal cavity) or operative laparoscopy (endoscopic surgery of the abdominal cavity) may receive a one-time lavage with the composition at the conclusion of the procedure to prevent adhesion formation. A woman patient plagued with chronic endometriosis may similarly be treated according to the above method. At the time of operative laparoscopy (with or without laser ablation), a composition of this invention may be used to lavage the abdominal cavity to prevent adhesion formation.

The following examples are provided for purposes of illustration, not limitation.

EXAMPLES

Example 1

Omega Fatty Acid Formulations

In this example, the formulations of various omega fatty compositions of the present invention are disclosed. In the following compositions, the omega-3 fatty acids, eicosapentaenoic acid and docosahexaenoic acid, are referred to as "EPA" and DHA," respectively, and the omega-6 fatty acids, gamma-linolenic acid and dihomo-gamma-linolenic acid are referred to as "GLA" and "DHGLA," respectively. The compositions may be formulated by mixing the following ingredients according to the weight percentages shown.

| A. Omega-3 Fatty Acid Compositions | |
|---|---|
| Formulation I: | |
| EPA | 30–50% |
| DHA | 5–10% |
| Polyethylene fatty acid esters | 2–8% |
| Dextrose | 2–4% |
| Acceptable carriers and/or diluents | 30–60% |
| Formulation II: | |
| EPA | 30–50% |
| DHA | 5–10% |
| Polyethylene fatty acid esters | 2–8% |
| Dextrose | 2–4% |
| Salicylate | 0.5–1% |
| Acceptable carriers and/or diluents | 30–60% |
| Formulation III: | |
| EPA | 30–50% |
| DHA | 5–10% |
| Polyethylene fatty acid esters | 2–8% |
| Dextrose | 2–4% |
| Vitamin A | 1–2% |
| Acceptable carriers and/or diluents | 30–60% |
| Formulation IV: | |
| EPA | 30–50% |
| DHA | 5–10% |
| Polyethylene fatty acid esters | 2–8% |
| Dextrose | 2–4% |
| Salicylate | 0.5–1% |
| Vitamin A | 1–2% |
| Acceptable carriers and/or diluents | 30–60% |
| Formulation V: | |
| EPA | 30–50% |
| DHA | 5–10% |
| Polysorbate | 2–8% |
| Salicylate | 0.5–1% |
| Vitamin A | 1–2% |
| Acceptable carriers and/or diluents | 30–60% |
| Formulation VI: | |
| EPA | 30–50% |
| DHA | 5–10% |
| Vitamin A | 1–2% |
| Pectin and/or Gelatin | 20–35% |
| Sodium Carboxymethylcelluose | 5–10% |
| (Dispersed in a plasticized hydrocarbon gel composed of 5% poly- | |

-continued

| ethylene in mineral oil) | |
|---|---|
| Flavoring | 0.5–1% |
| Acceptable carriers and/or diluents | 30–60% |

B. Omega-6 Fatty Acid Compositions

Formulation VII:

| | |
|---|---|
| GLA and/or DHGLA | 30–50% |
| Polyethylene fatty acid esters | 2–8% |
| Dextrose | 2–4% |
| Acceptable carriers and/or diluents | 30–60% |

Formulation VIII:

| | |
|---|---|
| GLA and/or DHGLA | 30–50% |
| Polyethylene fatty acid esters | 2–8% |
| Dextrose | 2–4% |
| Salicylate | 0.5–1% |
| Acceptable carriers and/or diluents | 30–60% |

Formulation IX:

| | |
|---|---|
| GLA and/or DHGLA | 30–50% |
| Polyethylene fatty acid esters | 2–8% |
| Dextrose | 2–4% |
| Vitamin A | 1–2% |
| Acceptable carriers and/or diluents | 30–60% |

Formulation X:

| | |
|---|---|
| GLA and/or DHGLA | 30–50% |
| Polyethylene fatty acid esters | 2–8% |
| Dextrose | 2–4% |
| Salicylate | 0.5–1% |
| Vitamin A | 1–2% |
| Acceptable carriers and/or diluents | 30–60% |

Formulation XI:

| | |
|---|---|
| GLA and/or DHGLA | 30–50% |
| Polysorbate | 2–8% |
| Salicylate | 0.5–1% |
| Vitamin A | 1–2% |
| Acceptable carriers and/or diluents | 30–60% |

Formulation XII:

| | |
|---|---|
| GLA and/or DHGLA | 30–50% |
| Vitamin A | 1–2% |
| Pectin and/or Gelatin | 20–35% |
| Sodium Carboxymethylceluose (Dispersed in a plasticized hydrocarbon gel composed of 5% polyethylene in mineral oil) | 5–10% |
| Flavoring | 0.5–1% |
| Acceptable carriers and/or diluents | 30–60% |

C. Omega-3 and Omega-6 Fatty Acid Compositions

Formulation XIII:

| | |
|---|---|
| EPA | 15–25% |
| DHA | 5–10% |
| GLA and/or DHGL | 15–25% |
| Polyethylene fatty acid esters | 2–8% |
| Dextrose | 2–4% |
| Acceptable carriers and/or diluents | 30–60% |

Formulation XIV:

| | |
|---|---|
| EPA | 15–25% |
| DHA | 5–10% |
| GLA and/or DHGL | 15–25% |
| Polysorbate | 2–8% |
| Acceptable carriers and/or diluents | 30–60% |

Formulation XV:

| | |
|---|---|
| GLA and/or DHGLA | 20–30% |
| EPA | 10–20% |
| DHA | 5–10% |
| Vitamin A | 1–2% |
| Pectin and/or Gelatin | 20–35% |
| Sodium Carboxymethylceluose (Dispersed in a plasticized hydrocarbon gel composed of 5% polyethylene in mineral oil) | 5–10% |
| Flavoring | 0.5–1% |
| Acceptable carriers and/or diluents | 30–60% |

Formulation XVI:

| | |
|---|---|
| GLA and/or DHGLA | 20–30% |
| EPA | 10–20% |
| DHA | 5–10% |
| Vitamin A | 1–2% |
| Pectin and/or Gelatin | 20–35% |
| Sodium Carboxymethylceluose (Dispersed in a plasticized hydrocarbon gel composed of 5% polyethylene in mineral oil) | 5–10% |
| Flavoring | 0.5–1% |
| Acceptable carriers and/or diluents | 30–60% |

Example 2

Inhibition of Inflammation

Two patients with inflammatory joint disease are plagued with chronically painful, swollen knees. Both patients are taking several oral anti-inflammatory agents, but still suffer from active disease. For the first patient, 1 to 3 ml of a liquid formulation of a composition of this invention is injected directly into the joint cavity. For the second patient, 500–1000 ml of the same formulation is used to lavage the joint space. Both patients experience improved symptoms, and the treatment is repeated every one to two months as needed.

Example 3

A 16-year-old girl who has active ulcerative colitis, a type of inflammatory bowel disease, is allergic to sulfa compounds (the commonly used drug to treat this condition is azulfidine). Prior to the present invention, the only other acceptable treatment plan would be high doses of corticosteroids. However, those compounds can produce serious systemic side effects, such as stunted growth, fluid retention, osteoporosis, increased risk of infection, and hypertension. Accordingly, a liquid formulation of a composition of this invention is administered in the form of a retention enema for 2 to 4 hours. This is repeated on a daily basis for two weeks, resulting in improved symptoms. If significant symptoms persist, the formulation is applied directly through a colonoscope at the time of examination, thereby dispersing composition through the entire colon as the colonoscope is slowly removed.

Example 4

A patient with carcinoma of the colon undergoes a colon resection for removal of the tumor. The surgeon is concerned that post-operative adhesion formation might occur, thereby placing the patient at significant risk for developing a bowel obstruction. Therefore, the surgeon, prior to closing the abdominal cavity, instills directly into the abdomen, 1000 ml of a liquid formulation of a composition of this invention. This is allowed to bathe the tissue for a period of 5 minutes, after which time it is removed by suction, and the abdomen is then closed.

Example 5

A woman is undergoing operative laparoscopy (with or without laser for endometriosis). This condition results from islands of endometrial tissue that become implanted outside the uterine cavity within the abdomen. After ablation of this abnormal tissue at the time of surgery, the surgeon wishes to minimize adhesion formation (which is particularly important in the pelvic area, because adhesions here can in themselves produce significant pain and infertility). Five hundred to 1000 mls of a liquid formulation of a composition of this invention is introduced through the laparoscope into the abdominal cavity. This is allowed to bathe the tissue for a period of 5 minutes, after which time it is removed by suction prior to removal of the laparoscope and closure.

Example 6

Interstitial cystitis is a painful chronic inflammatory condition of the bladder of unknown cause for which current modes of therapy are not effective. Patients suffering from this condition are treated by the composition of this invention by instilling, either directly through a cystoscope or via foley catheter, 100 to 500 mls of a liquid formulation of the composition into the bladder cavity. The fluid remains in the bladder until it is expelled through urination, or drained by the surgeon. Treatment is then repeated every two to four weeks as needed.

From the foregoing, it will be appreciated that, although specific embodiments of this invention have been described herein for the purposes of illustration, various modifications may be made without departing from the spirit and scope of the invention. Accordingly, the invention is not limited except by the appended claims.

We claim:

1. A method for inhibiting tissue adhesion in a body cavity of a warm-blooded animal, comprising administering to the body cavity an effective amount of a composition comprising an omega fatty acid, a nonionic surfactant, a cyclooxygenase inhibitor, and a pharmaceutically acceptable carrier or diluent.

2. The method of 1 wherein the body cavity is selected from the group consisting of oral, abdominal, pleural, thoracic, pericardial, joint, rectal, bladder, and tympanic cavities.

3. The method of claim 1 wherein the omega fatty acid is an omega-3 fatty acid.

4. The method of claim 1 wherein the omega fatty acid is an omega-6 fatty acid.

5. The method of claim 1 wherein the omega fatty acid is a mixture of an omega-3 fatty acid and an omega-6 fatty acid.

6. The method of claim 3 wherein the omega-3 fatty acid is selected from the group consisting of eicosapentaenoic acid, docosahexaenoic acid, and mixtures thereof.

7. The method of claim 4 wherein the omega-6 fatty acid is selected from the group consisting of gamma-linolenic acid, dihomo-gamma-linolenic acid, and mixtures thereof.

8. The method of claim 1 wherein the nonionic surfactant component a polyethylene fatty acid ester.

9. The method of claim 8 wherein the polyethylene fatty acid ester is polysorbate.

10. The method of claim 1 wherein the cyclooxygenase inhibitor is a salicylate.

11. The method of claim 1 wherein the composition further comprises vitamin A.

12. A method for inhibiting scar formation in a body cavity of warm-blooded animal, comprising administering to the body cavity an effective amount of a composition comprising an omega fatty acid, a nonionic surfactant, a cyclooxygenase inhibitor, and a pharmaceutically acceptable carrier or diluent.

13. The method of 12 wherein the body cavity is selected from the group consisting of oral, abdominal, pleural, thoracic, pericardial, joint, rectal, bladder, and tympanic cavities.

14. The method of claim 12 wherein the omega fatty acid is an omega-3 fatty acid.

15. The method of claim 12 wherein the omega fatty acid is an omega-6 fatty acid.

16. The method of claim 12 wherein the omega fatty acid is a mixture of an omega-3 fatty acid and an omega-6 fatty acid.

17. The method of claim 14 wherein the omega-3 fatty acid is selected from the group consisting of eicosapentaenoic acid, docosahexaenoic acid, and mixtures thereof.

18. The method of claim 15 wherein the omega-6 fatty acid is selected from the group consisting of gamma-linolenic acid, dihomo-gamma-linolenic acid, and mixtures thereof.

19. The method of claim 12 wherein the nonionic surfactant component a polyethylene fatty acid ester.

20. The method of claim 19 wherein the polyethylene fatty acid ester is polysorbate.

21. The method of claim 12 wherein the cyclooxygenase inhibitor is a salicylate.

22. The method of claim 12 wherein the composition further comprises vitamin A.

23. A method for inhibiting tissue adhesion in a body cavity of a warm-blooded animal, comprising administering to the body cavity an effective amount of a composition comprising an omega fatty acid, a nonionic surfactant, a cyclooxygenase inhibitor, vitamin A, and a pharmaceutically acceptable carrier or diluent.

24. A method for inhibiting scar formation in a body cavity of a warm-blooded animal, comprising administering to the body cavity an effective amount of a composition comprising an omega fatty acid, a nonionic surfactant, a cyclooxygenase inhibitor, vitamin A, and a pharmaceutically acceptable carrier or diluent.

* * * * *